(12) United States Patent
Ku et al.

(10) Patent No.: US 6,608,216 B2
(45) Date of Patent: Aug. 19, 2003

(54) PROCESS FOR THE PREPARATION OF CHIRAL GLUCOCORTICOID RECEPTOR AGENTS

(75) Inventors: Yi-Yin Ku, Buffalo Grove, IL (US); Tim Grieme, Chicago, IL (US); Howard E. Morton, Gurnee, IL (US); Steven A. King, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/184,572

(22) Filed: Jun. 28, 2002

(65) Prior Publication Data

US 2003/0073844 A1 Apr. 17, 2003

Related U.S. Application Data

(60) Provisional application No. 60/302,448, filed on Jun. 29, 2001.

(51) Int. Cl.$^7$ .................. C07D 311/78; C07D 311/80
(52) U.S. Cl. ........................ 549/384; 549/390
(58) Field of Search .................. 549/384, 390

(56) References Cited

FOREIGN PATENT DOCUMENTS

| WO | 9619458 | 6/1996 |
|----|---------|--------|
| WO | 9838193 | 9/1998 |
| WO | 9941256 | 8/1999 |

*Primary Examiner*—Taofiq Solola
(74) *Attorney, Agent, or Firm*—Christopher P. Rogers

(57) ABSTRACT

The present invention relates to the preparation of chiral glucocorticoid receptor agents via biaryl atropisomers.

27 Claims, No Drawings

PROCESS FOR THE PREPARATION OF CHIRAL GLUCOCORTICOID RECEPTOR AGENTS

This application claims priority to the provisional application Serial No. 60/302,448 filed on Jun. 29, 2001.

TECHNICAL FIELD

The present invention relates to a novel process for the preparation of chiral selective glucocorticoid receptor agents.

BACKGROUND OF THE INVENTION

The glucocorticoid receptor (GR) has an essential role in regulating human physiology and immune response. Steroids which interact with GR have been shown to be potent antiinflammatory agents. Steroidal GR ligands, however, have side effects associated with chronic dosing believed to be the result of cross-reactivity with other steroid receptors such as estrogen, progesterone, androgen, and mineralocorticoid receptors which have somewhat homologous ligand binding domains. Therefore, nonsteroidal agents selective for GR are actively being researched for the treatment of inflammation, inflamatory disease, immune and autoimmune diseases.

SUMMARY OF THE INVENTION

The present invention is directed to a process for preparing biaryl atropisomers that are used to prepare chiral GR agents. The process proceeds through a chirality transfer from a stereogenic center of a secondary alcohol to the biaryl stereogenic axis via regioselective intramolecular migration. This methodology allows for the preparation of a single biaryl atropisomer in high yield with high diastereoselectivity which subsequently leads to the synthesis of chiral glucocorticoid receptor agents.

In particular, the process is used to prepare chiral 5-substituted-2,2,4-trimethyl-2,5-dihydro-1H-chromeno[3,4-f]quinolines wherein (5S)-5-allyl-10-methoxy-2,2,4-trimethyl-2,5-dihydro-1H-chromeno[3,4-f]quinoline is a preferred chiral GR agent.

DETAILED DESCRIPTION OF THE PRESENT INVENTION

The present invention is directed to a process for the preparation of biaryl atropisomers that can be used for preparation of compounds of formula (I)

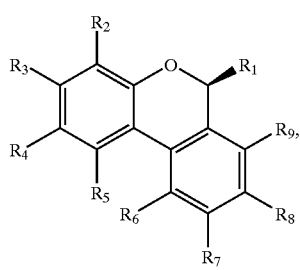

(I)

wherein
  $R_1$ is selected from alkenyl, alkyl, alkynyl and aryl, wherein alkenyl is preferred and wherein allyl is most preferred;
  $R_2$, $R_3$ and $R_4$ are each independently selected from hydrogen, alkoxy, alkenyl, alkyl, alkynyl, aryl and halogen; or
  $R_2$ and $R_3$ or $R_3$ and $R_4$ together with the carbon atoms to which they are attached, together form a ring wherein the ring is selected from aryl, cycloalkyl and heterocycle, wherein hydrogen is preferred for each of $R_2$, $R_3$ and $R_4$;
  $R_5$ is selected from hydrogen, alkenyl, alkenyloxy, alkoxy, alkoxycarbonyloxy, alkoxysulfonyloxy, alkyl, alkylcarbonyloxy, alkylsulfonyloxy, alkynyl, alkynyloxy, aryl, arylalkoxy, arylalkoxycarbonyloxy, aryloxy, arylsulfonyloxy, haloalkoxy, haloalkylcarbonyloxy, haloalkylsulfonyloxy, halogen, heterocycle and $(NR_CR_D)$carbonyloxy, wherein alkoxy and haloalkylsulfonyl are preferred and wherein methoxy and trifluoromethanesulfonate are most preferred;
  $R_C$ and $R_D$ are each independently selected from hydrogen and alkyl;
  $R_6$, $R_7$, $R_8$ and $R_9$ are each independently selected from hydrogen, alkoxy, alkenyl, alkyl, alkynyl, aryl and halogen; or
  $R_6$ and $R_7$ or $R_7$ and $R_8$ or $R_8$ and $R_9$ together with the carbon atoms to which they are attached, together form a ring wherein the ring is selected from aryl, cycloalkyl and heterocycle, wherein hydrogen is preferred for each of $R_6$ and $R_7$; $R_8$ and $R_9$ together with the carbon atoms to which they are attached, together form a ring wherein the ring is a heterocycle is preferred and wherein $R_8$ and $R_9$ together with the carbon atoms to which they are attached, together form a ring wherein the ring 4,6,6-trimethyl-1,2,3,6-tetrahydropyridinyl is most preferred;
wherein the process comprises the steps of:
  (a) treating a compound of formula (Ia)

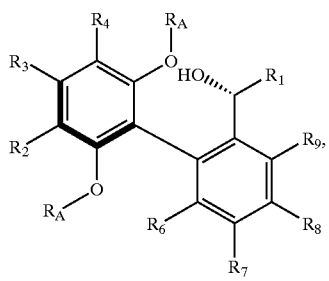

(Ia)

with a base in a first solvent wherein $R_A$ is a hydroxy protecting group;
  (b) treating the product of step (a) with an electrophile to provide a compound of formula (Ib);

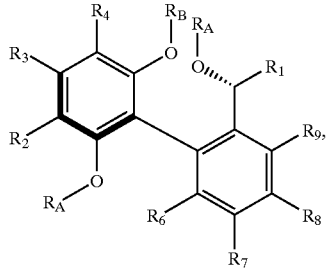

(Ib)

wherein $R_B$ is selected from alkoxycarbonyl, alkoxysulfonyl, alkenyl, alkyl, alkylcarbonyl, alkylsulfonyl, alkynyl, arylalkoxycarbonyl, arylalkyl, arylsulfonyl, haloalkyl, haloalkylcarbonyl, haloalkylsulfonyl and (NR$_C$R$_D$)carbonyl, wherein alkyl and haloalkylsulfonyl are preferred and methyl and trifluoromethylsulfonyl are most preferred; R$_C$ and R$_D$ are each independently selected from hydrogen and alkyl;

(c) treating the compound of formula (Ib) with a hydroxy deprotecting reagent in a second solvent to provide a compound of formula (Ic); and

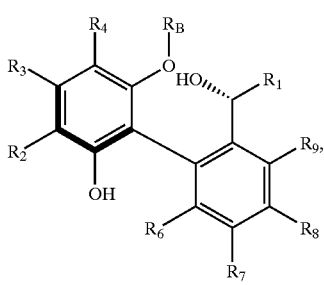

(Ic)

(d) treating the compound of formula (Ic) with an azo reagent and a phosphine reagent in a third solvent to provide the compound of formula (I).

According to another embodiment, the present invention further comprises the steps of the process described above wherein step (a) is conducted from about −5° C. to about 25° C.; isolating the product of step (b) by pouring step (b) into saturated ammonium chloride solution; stirring the solution; separating the aqueous phase from the organic phase; washing the organic phase with brine; drying the organic phase over sodium sulfate; concentrating the organic phase to provide an oil; dissolving the oil in heptane; extracting the heptane with acetonitrile; treating the heptane with charcoal; and concentrating the heptane to provide a compound of formula (Ib); step (c) is conducted between 18° C. and about 25° C. for about 12 to 36 hours; isolating the product of step (c) by pouring step (c) into a saturated solution of ammonium chloride; stirring the solution; adding tert-butyl methyl ether to the solution; stirring the solution for about 5 to 20 minutes; separating the aqueous phase from the organic phase; washing the organic phase with brine; drying the organic phase over sodium sulfate; concentrating the organic phase to provide a solid; suspending the solid in isopropanol:heptane 1:12.5 for 1 to 3 hours; cooling the isopropanol:heptane 1:12.5 to −5° C. to about 5° C.; and filtering the isopropanol:heptane 1:12.5 to provide a compound of formula (Ic); in step (d) the product of step (c) and the triphenylphosphine are dissolved in the tetrahydrofuran at a temperature between 18° C. and about 25° C.; the tetrahydrofuran may optionally be cooled to about −5° C. to about 15° C.; and the diisobutyl azodicarboxylate is added to the tetrahydrofuran over about 0.25 to 3 hours while maintaining the temperature of the tetrahydrofuran from −5° C. to about 25° C.; isolating the product from step(d) by concentrating the tetrahydrofuran to about ¼ to ⅓ of original volume; adding heptane to the tetrahydrofuran; cooling the tetrahydrofuran/heptane mixture to about −5° C. to about 5° C.; allowing the tetrahydrofuran/heptane mixture to stand for 12 to 24 hours; filtering the tetrahydrofuran/heptane mixture; repeating concentration, cooling and filtering until small amount of solid precipitates out of the tetrahydrofuran/heptane mixture; concentrating the tetrahydrofuran/heptane mixture to provide crude product of step (d); purifying the crude product of step (d) by flash chromatography to provide the product of step (d); and recrystallizing the product of step (d) from isopropanol.

The process of the present invention is particularly useful for preparing (5S)-5-allyl-10-methoxy-2,2,4-trimethyl-2,5-dihydro-1H-chromeno[3,4-f]quinoline and (5S)-5-allyl-2,2,4-trimethyl-2,5-dihydro-1H-chromeno[3,4-f]quinolin-10-yl trifluoromethanesulfonate.

According to yet another embodiment, the present invention discloses a process for the preparation of a compound having formula (II)

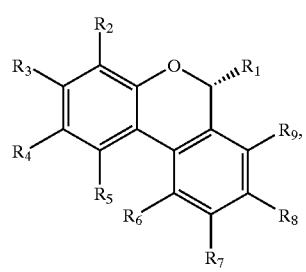

(II)

wherein
R$_1$ is selected from selected from the group consisting of alkenyl, alkyl, alkynyl and aryl;
R$_2$, R$_3$ and R$_4$ are each independently selected from the group consisting of hydrogen, alkoxy, alkenyl, alkyl, alkynyl and halogen; or
R$_2$ and R$_3$ or R$_3$ and R$_4$ together with the carbon atoms to which they are attached, together form a ring wherein the ring is selected from the group consisting of aryl, cycloalkyl and heterocycle;
R$_5$ is selected from the group consisting of hydrogen, alkenyl, alkenyloxy, alkoxy, alkoxycarbonyloxy, alkoxysulfonyloxy, alkyl, alkylcarbonyloxy, alkylsulfonyloxy, alkynyl, alkynyloxy, aryl, arylalkoxy, arylalkoxycarbonyloxy, arylsulfonyloxy, haloalkoxy, haloalkylcarbonyloxy, haloalkylsulfonyloxy, halogen, heterocycle and (NR$_C$R$_D$)carbonyloxy; and
R$_6$, R$_7$, R$_8$ and R$_9$ are each independently selected from the group consisting of hydrogen, alkoxy, alkenyl, alkyl, alkynyl and halogen; or
R$_6$ and R$_7$ or R$_7$ and R$_8$ or R$_8$ and R$_9$ together with the carbon atoms to which they are attached, together form a ring wherein the ring is selected from the group consisting of aryl, cycloalkyl and heterocycle;
wherein said process comprises the steps of:
(a) treating a compound of formula (IIa)

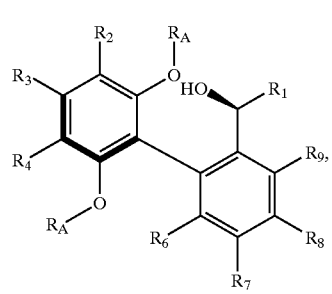

(IIa)

with a base in a first solvent, wherein R$_A$ is a hydroxy protecting group and R$_1$, R$_2$, R$_3$, R$_4$, R$_6$, R$_7$, R$_8$ and R$_9$ are as defined above (b) treating the product of step (a) with an electrophile to provide a compound of formula (IIb)

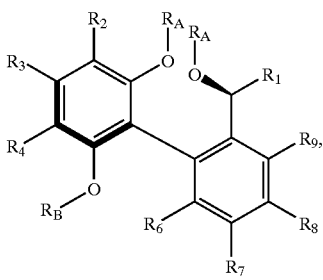

(IIb)

wherein $R_B$ is selected from the group consisting of alkoxycarbonyl, alkoxysulfonyl, alkenyl, alkyl, alkylcarbonyl, alkylsulfonyl, alkynyl, arylalkoxycarbonyl, arylalkyl, arylsulfonyl, haloalkyl, haloalkylcarbonyl, haloalkylsulfonyl and $(NR_CR_D)$carbonyl wherein $R_C$ and $R_D$ are selected from the group consisting of hydrogen and alkyl; and $R_A$, $R_1$, $R_2$, $R_3$, $R_4$, $R_6$, $R_7$, $R_8$ and $R_9$ are as defined above;

(c) treating the compound of formula (IIb) with a hydroxy deprotecting reagent in a second solvent to provide a compound of formula (IIc)

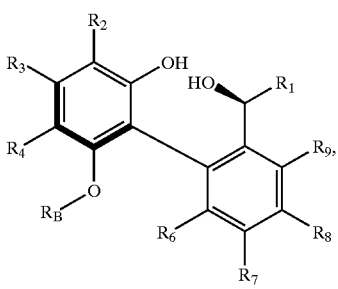

(IIc)

wherein $R_B$, $R_1$, $R_2$, $R_3$, $R_4$, $R_6$, $R_7$, $R_8$ and $R_9$ are as defined above; and (d) treating the compound of formula (IIc) with an azo reagent and a phosphine reagent in a third solvent to provide the compound of formula (II).

According to a further embodiment, the present invention discloses a process for the preparation of a compound having formula (I)

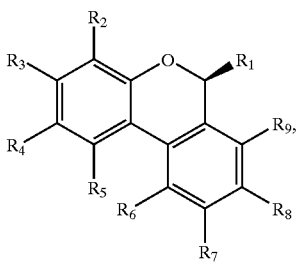

(I)

wherein $R_1$ is selected from the group consisting of alkenyl, alkyl, alkynyl and aryl, wherein alkenyl is preferred and wherein allyl is most preferred;

$R_2$, $R_3$ and $R_4$ are each independently selected from the group consisting of hydrogen, alkoxy, alkenyl, alkyl, alkynyl, aryl and halogen; or $R_2$ and $R_3$ or $R_3$ and $R_4$ together with the carbon atoms to which they are attached, together form a ring wherein the ring is selected from the group consisting of aryl, cycloalkyl and heterocycle, wherein hydrogen is preferred for each of $R_2$, $R_3$ and $R_4$;

$R_5$ is selected from the group consisting of hydrogen, alkenyl, alkenyloxy, alkoxy, alkoxycarbonyloxy, alkoxysulfonyloxy, alkyl, alkylcarbonyloxy, alkylsulfonyloxy, alkynyl, alkynyloxy, aryl, arylalkoxy, arylalkoxycarbonyloxy, aryloxy, arylsulfonyloxy, haloalkoxy, haloalkylcarbonyloxy, haloalkylsulfonyloxy, halogen, heterocycle and $(NR_CR_D)$carbonyloxy, wherein alkoxy is preferred and methoxy is most preferred;

$R_C$ and $R_D$ are each independently selected from hydrogen and alkyl; and $R_6$, $R_7$, $R_8$ and $R_9$ are each independently selected from the group consisting of hydrogen, alkoxy, alkenyl, alkyl, alkynyl, aryl and halogen; or $R_6$ and $R_7$ or $R_7$ and $R_8$ or $R_8$ and $R_9$ together with the carbon atoms to which they are attached, together form a ring wherein the ring is selected from the group consisting of aryl, cycloalkyl and heterocycle, wherein hydrogen is preferred for each of $R_6$ and $R_7$; $R_8$ and $R_9$ together with the carbon atoms to which they are attached, together form a ring wherein the ring is a heterocycle is preferred, wherein $R_8$ and $R_9$ together with the carbon atoms to which they are attached, together form a ring wherein the ring 4,6,6-trimethyl-1,2,3,6-tetrahydropyridinyl is most preferred;

wherein said process comprises the steps of:

(a) treating a compound of formula (Ia)

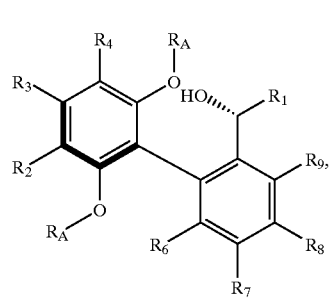

(Ia)

with at least two molar equivalents of a hydroxy deprotecting reagent in a first solvent, wherein $R_A$ is a hydroxy protecting group and $R_1$, $R_2$, $R_3$, $R_4$, $R_6$, $R_7$, $R_8$ and $R_9$ are as defined above, to provide a compound of formula (Ia) wherein $R_A$ is hydrogen;

(b) treating the product of step (a) with an azo reagent and a phosphine reagent in a second solvent, a preferred second solvent is tetrahydrofuran.

As used throughout this specification and the appended claims, the following terms have the following meanings:

The term "single biaryl atropisomer" as used herein, refers to a biaryl atropisomer of general formula (Ib) or (IIb) shown below:

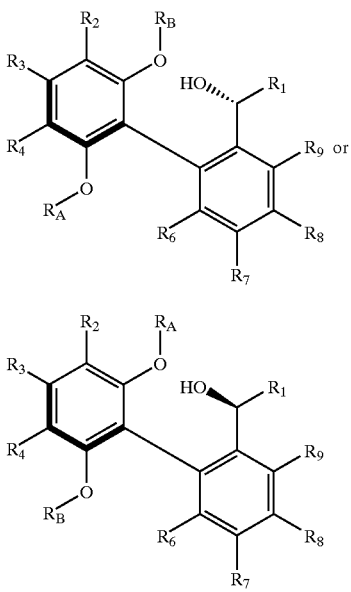

wherein $R_1$, $R_2$, $R_3$, $R_4$, $R_6$, $R_7$, $R_8$ and $R_9$ are as defined in formula (I) for a biaryl atropisomer of general formula (Ib); $R_1$, $R_2$, $R_3$, $R_4$, $R_6$, $R_7$, $R_8$ and $R_9$ are as defined in formula (II) for a biaryl atropisomer of general formula (IIb); $R_A$ is a hydroxy protecting group and $R_B$ is selected from alkoxycarbonyl, alkoxysulfonyl, alkenyl, alkyl, alkylcarbonyl, alkylsulfonyl, alkynyl, arylalkoxycarbonyl, arylalkyl, arylsulfonyl, haloalkyl, haloalkylcarbonyl, haloalkylsulfonyl and $(NR_CR_D)$carbonyl.

The term "azo reagent" as used herein, refers to a reagent, R—N=N—R, wherein R is selected from alkoxycarbonyl and cycloalkyloxycarbonyl. Representative examples of azo reagent include, but are not limited to, diethyl azodicarboxylate, di-tert-butyl azodicarboxylate, diisopropyl azodicarboxylate, dimethyl azodicarboxylate and dicyclohexyl azodicarboxylate. A preferred azo reagent is selected from diethyl azodicarboxylate, di-tert-butyl azodicarboxylate and diisopropyl azodicarboxylate. A most preferred azo reagent is diisopropyl azodicarboxylate.

The term "base" as used herein, refers to any molecular moiety that can remove the hydrogen from a secondary alcohol. Representative examples of base include, but are not limited to, alkoxides such as sodium methoxide, sodium ethoxide, potassium methoxide, potassium ethoxide and potassium tert-butoxide; hydrides such as sodium hydride, potassium hydride and lithium hydride; amides such as lithium diisopropylamide, lithium bis(trimethylsilyl)amide, potassium bis(trimethylsilyl)amide and sodium bis(trimethylsilyl)amide. A preferred base is potassium tert-butoxide.

The term "electrophile" as used herein, refers to any molecular moiety that contains a carbon atom or a sulfur atom wherein the carbon or sulfur atom can accept a pair of electrons. Representative examples of electrophile include, but are not limited to, methyltriflate, methyltosylate, dimethylsulfate and trifluoro-N-phenyl-N-[(trifluoromethyl)sulfonyl]methanesulfonamide; acid chlorides such as acetyl chloride, propionyl chloride, trimethylacetyl chloride and dimethylcarbamyl chloride; alkenyl halides such as allyl bromide; alkyl halides such as iodomethane, iodoethane, trifluoromethyl iodide, perfluoroethyl iodide, benzyl bromide and benzyl chloride; alkynyl halides such as propargyl bromide; anhydrides such as acetic anhydride, trifluoromethyl anhydride and di-tert-butyl dicarbonate; chloroformates such as benzyl chloroformate, ethyl chloroformate and isopropyl chloroformate; sulfonyl chlorides such as methanesulfonyl chloride (mesyl chloride), para-toluenesulfonyl chloride (tosyl chloride) and phenylsulfonyl chloride; and sulfonic anhydrides such as trifluoromethanesulfonic anhydride (triflic anhydride). A preferred electrophile is selected from trifluoro-N-phenyl-N-[(trifluoromethyl)sulfonyl]methanesulfonamide and iodomethane.

The term "hydroxy protecting group" as used herein, refers to a substituent which protects hydroxyl groups against undesirable reactions during synthetic procedures. Preferred hydroxy protecting groups of the present invention include, but are not limited to, alkylcarbonyl, (alkyl)(diaryl)silyl, (trialkyl)silyl, (triaryl)silyl and (triarylalkyl)silyl. Representative examples of hydroxy protecting groups include, but are not limited to, acetyl, ethylcarbonyl, propylcarbonyl, tert-butylcarbonyl, trimethylsilyl, triethylsilyl, triisopropylsilyl, dimethylisopropylsilyl, diethylisopropylsilyl, tert-butyldimethylsilyl, methyldiphenylsilyl, tert-butyldiphenylsilyl, tribenzylsilyl and triphenylsilyl. A preferred hydroxy protecting group is tert-butyldimethylsilyl.

The term "hydroxy deprotecting reagent" as used herein, refers to a reagent that removes a hydroxy protecting group. Representative examples of hydroxy deprotecting reagents includes, but is not limited to, a source of fluoride anion such as tetrabutylammonium fluoride, potassium fluoride and hydrogen fluoride; inorganic acids such as hydrochloric acid and hydrobromic acid; organic acids such as acetic acid and trifluoroacetic acid; a source of aqueous hydroxide ion such as aqueous potassium hydroxide, aqueous sodium hydroxide, aqueous potassium carbonate and aqueous sodium bicarbonate. A preferred hydroxy deprotecting reagent is tetrabutylammonium fluoride.

The term "phosphine reagent" as used herein refers to $(R_E)_3P$ wherein RE is selected from alkyl and aryl. Representative example of $(R_E)_3P$ include, but are not limited to, tributylphosphine, tri-tert-butylphosphine, triisobutylphosphine, triisopropylphosphine, tripropylphosphine, triethylphosphine, trimethylphosphine, tris(4-methylphenyl)phosphine, tris(4-methoxyphenyl)phosphine, tris(4-chlorophenyl)phosphine, tris(4-bromophenyl)phosphine and triphenylphosphine. A preferred phosphine reagent is triphenylphosphine.

The term "first solvent" as used herein, refers to any organic solvent that will allow the reaction in step (a) and the reaction in step (b) to proceed to completion or substantially to completion. A preferred first solvent is tetrahydrofuran.

The term "second solvent" as used herein, refers to any organic solvent that will allow the reaction in step (c) to proceed to completion or substantially to completion. A preferred second solvent is tetrahydrofuran.

The term "third solvent" as used herein, refers to any organic solvent that will allow the reaction in step (d) to proceed to completion or substantially to completion. A preferred third solvent is tetrahydrofuran.

The term "alkenyl" as used herein, refers to a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenyloxy" as used herein, refers to an alkenyl group, as defined herein, appended to the parent molecular moiety through an oxygen atom. Representative examples of alkenyloxy include, but are not limited to, allyloxy, 2-butenyloxy and 3-butenyloxy.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonyloxy" as used herein, refers to an alkoxycarbonyl group, as defined herein, appended to the parent molecular moiety through an oxygen atom. Representative examples of alkoxycarbonyloxy include, but are not limited to, methoxycarbonyloxy, ethoxycarbonyloxy, and tert-butoxycarbonyloxy.

The term "alkoxysulfonyl" as used herein, refers to an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkoxysulfonyloxy" as used herein, refers to an alkoxysulfonyl group, as defined herein, appended appended to the parent molecular moiety through an oxygen atom. Representative examples of alkoxysulfonyloxy include, but are not limited to, methoxysulfonyloxy, ethoxysulfonyloxy and propoxysulfonyloxy.

The term "alkyl" as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" as used herein, refers to an alkylcarbonyl group, as defined herein, appended to the parent molecular moiety through an oxygen atom. Representative examples of alkylcarbonyloxy include, but are not limited to, acetyloxy, propionyloxy and (2,2-dimethylpropanoyl)oxy.

The term "alkylsulfonyl" as used herein, refers to an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylsulfonyloxy" as used herein, refers to an alkylsulfonyl group, as defined herein, appended to the parent molecular moiety through an oxygen atom. Representative examples of alkylsulfonyloxy include, but are not limited to, methylsulfonyloxy and ethylsulfonyloxy.

The term "alkynyl" as used herein, refers to a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkynyloxy" as used herein, refers to an alkynyl group, as defined herein, appended to the parent molecular moiety through an oxygen atom. Representative examples of alkynyloxy include, but are not limited to, 2-propynyloxy and 2-butynyloxy.

The term "aryl" as used herein, refers to a phenyl group. The aryl groups of this invention can be substituted with 1, 2, or 3 substituents independently selected from alkenyl, alkoxy, alkoxycarbonyl, alkoxysulfonyl, alkyl, alkylcarbonyl, alkynyl, cyano, haloalkoxy, haloalkyl, halogen, nitro, —$NR_{C}R_{D}$ and ($NR_{C}R_{D}$)carbonyl.

The term "arylalkoxy" as used herein, refers to an aryl group, as defined herein, appended to the parent molecular moiety through an alkoxy group, as defined herein. Representative examples of arylalkoxy include, but are not limited to, benzyloxy, 2-phenylethoxy and 5-phenylpentyloxy.

The term "arylalkoxycarbonyl" as used herein, refers to an arylalkoxy group, as defined herein, appended to the parent molecular moiety through a carbonyl group, as defined herein. Representative examples of arylalkoxycarbonyl include, but are not limited to, benzyloxycarbonyl.

The term "arylalkoxycarbonyloxy" as used herein, refers to an arylalkoxycarbonyl group, as defined herein, appended to the parent molecular moiety through an oxygen atom. Representative examples of arylalkoxycarbonyloxy include, but are not limited to, benzyloxycarbonyloxy.

The term "arylalkyl" as used herein, refers to an aryl group, as defined herein, appended to the parent molecular moiety through an alkyl group, as defined herein. Representative examples of arylalkyl include, but are not limited to, benzyl and 2-phenylethyl.

The term "aryloxy" as used herein, refers to an aryl group, as defined herein, appended to the parent molecular moiety through an oxygen atom. Representative examples of aryloxy include, but are not limited to, phenoxy, 4-chlorophenoxy and 3,4-dimethylphenoxy.

The term "arylsulfonyl" as used herein, refers to an aryl group, as defined herein, appended to the parent molecular moiety through a sulfonyl group, as defined herein. Representative examples of arylsulfonyl include, but are not limited to, phenylsulfonyl and 4-methylphenylsulfonyl.

The term "arylsulfonyloxy" as used herein, refers to an arylsulfonyl group, as defined herein, appended to the parent molecular moiety through an oxygen atom. Representative examples of arylsulfonyloxy include, but are not limited to, phenylsulfonyloxy and 4-methylphenylsulfonyloxy.

The term "carbonyl" as used herein, refers to a —C(O)— group.

The term "cyano" as used herein, refers to a —CN group.

The term "cycloalkyl" as used herein, refers to a saturated cyclic hydrocarbon group containing from 4 to 6 carbons. Examples of cycloalkyl include cyclobutyl, cyclopentyl and cyclohexyl.

The term "cycloalkyloxy" as used herein, refers to cycloalkyl group, as defined herein, appended to the parent molecular moiety through an oxygen atom. Representative examples of cycloalkyloxy include, but are not limited to, cyclobutyloxy, and cyclohexyloxy.

The term "cycloalkyloxycarbonyl" as used herein, refers to cycloalkyloxy group, as defined herein, appended to the parent molecular moiety through a carbonyl group, as defined herein. Representative examples of cycloalkyloxycarbonyl include, but are not limited to, cyclohexyloxycarbonyl.

The term "halo" or "halogen" as used herein, refers to —Cl, —Br, —I or —F.

The term "haloalkoxy" as used herein, refers to at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl and pentafluoroethyl.

The term "haloalkylcarbonyl" as used herein, refers to a haloalkyl group, as defined herein, appended to the parent molecular moiety through a carbonyl group, as defined herein. Representative examples of haloalkylcarbonyl include, but are not limited to, trifluoromethylcarbonyl.

The term "haloalkylcarbonyloxy" as used herein, refers to a haloalkylcarbonyl group, as defined herein, appended to the parent molecular moiety through an oxygen atom. Representative examples of haloalkylcarbonyloxy include, but are not limited to, trifluoromethylcarbonyloxy.

The term "haloalkylsulfonyl" as used herein, refers to a haloalkyl group, as defined herein, appended to the parent molecular moiety through a sulfonyl group, as defined herein. Representative examples of haloalkylsulfonyl include, but are not limited to, trifluoromethylsulfonyl and pentafluoroethylsulfonyl.

The term "haloalkylsulfonyloxy" as used herein, refers to a haloalkylsulfonyl group, as defined herein, appended to the parent molecular moiety through an oxygen atom. Representative examples of haloalkylsulfonyloxy include, but are not limited to, trifluoromethylsulfonyloxy and pentafluoroethylsulfonyloxy.

The term "heterocycle" or "heterocyclic" as used herein, refers to a monocyclic or bicyclic ring system. Monocyclic ring systems are exemplified by any 3- or 4-membered ring containing a heteroatom independently selected from oxygen, nitrogen and sulfur; or a 5-6- or 7-membered ring containing one, two or three heteroatoms wherein the heteroatoms are independently selected from nitrogen, oxygen and sulfur. The 5-membered ring has from 0–2 double bonds and the 6- and 7-membered ring have from 0–3 double bonds. Representative examples of monocyclic ring systems include, but are not limited to, azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydropyridinyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl. Bicyclic ring systems are exemplified by any of the above monocyclic ring systems fused to an aryl group as defined herein, a cycloalkyl group as defined herein, or another monocyclic ring system. Representative examples of bicyclic ring systems include but are not limited to, for example, benzimidazolyl, benzodioxinyl, benzothiazolyl, benzothienyl, benzotriazolyl, benzoxazolyl, benzofuranyl, benzopyranyl, benzothiopyranyl, cinnolinyl, indazolyl, indolyl, 2,3-dihydroindolyl, indolizinyl, naphthyridinyl, isobenzofuranyl, isobenzothienyl, isoindolyl, isoquinolinyl, phthalazinyl, pyranopyridinyl, quinolinyl, quinolizinyl, quinoxalinyl, quinazolinyl, tetrahydroisoquinolinyl, tetrahydroquinolinyl, and thiopyranopyridinyl.

The heterocycles of this invention can be substituted with 1, 2, or 3 substituents independently selected from alkenyl, alkoxy, alkoxycarbonyl, alkoxysulfonyl, alkyl, alkylcarbonyl, alkynyl, cyano, haloalkoxy, haloalkyl, halogen, nitro, oxo, —$NR_CR_D$ and ($NR_CR_D$)carbonyl. Representative examples of substituted heterocycles includes, but is not limited to, 4,6,6-trimethyl-1,2,3,6-tetrahydropyridinyl.

The term "nitro" as used herein, refers to a —$NO_2$ group.

The term "—$NR_CR_D$" as used herein, refers to two groups, $R_C$ and $R_D$, which are appended to the parent molecular moiety through a nitrogen atom. $R_C$ and $R_D$ are each independently selected from hydrogen and alkyl. Representative examples of —$NR_CR_D$ include, but are not limited to, amino, methylamino, dimethylamino, ethylmethylamino and diethylamino.

The term "($NR_CR_D$)carbonyl" as used herein, refers to a —$NR_CR_D$ group, as defined herein, appended to the parent molecular moiety through a carbonyl group, as defined herein. Representative examples of ($NR_CR_D$)carbonyl include, but are not limited to, aminocarbonyl, (methylamino)carbonyl, (dimethylamino)carbonyl, (ethylmethylamino)carbonyl, and (diethylamino)carbonyl.

The term "($NR_CR_D$)carbonyloxy" as used herein, refers to a ($NR_CR_D$)carbonyl group, as defined herein, appended to the parent molecular moiety through an oxygen atom. Representative examples of ($NR_CR_D$)carbonyloxy include, but are not limited to, aminocarbonyloxy, (methylamino)carbonyloxy, (dimethylamino)carbonyloxy, (ethylmethylamino)carbonyloxy and (diethylamino)carbonyloxy.

The term "oxo" as used herein, refers to a =O moiety.

The term "sulfonyl" as used herein, refers to a —$SO_2$— group.

The term "(alkyl)(diaryl)silyl" as used herein, refers to an alkyl group, as defined herein, and two aryl groups, as defined herein, appended to the parent molecular moiety through a silane atom. Representative examples of (alkyl)(diaryl)silyl, include, but are not limited to, methyldiphenylsilyl and tert-butyldiphenylsilyl.

The term "(trialkyl)silyl" as used herein, refers to three independent alkyl groups, as defined herein, appended to the parent molecular moiety through a silane atom. Representative examples of (trialkyl)silyl, include, but are not limited to, trimethylsilyl, triethylsilyl, triisopropylsilyl, dimethylisopropylsilyl, diethylisopropylsilyl and tert-butyldimethylsilyl.

The term "(triaryl)silyl" as used herein, refers to three independent aryl groups, as defined herein, appended to the parent molecular moiety through a silane atom. Representative examples of (triaryl)silyl, include, but are not limited to, triphenylsilyl.

The term "(triarylalkyl)silyl" as used herein, refers to three independent arylalkyl groups, as defined herein, appended to the parent molecular moiety through a silane atom. Representative examples of (triarylalkyl)silyl, include, but are not limited to, tribenzylsilyl.

Synthetic Processes

Abbreviations which have been used in the descriptions of the Schemes and the Examples that follow are: t-Bu for tert-butyl; DIAD for diisopropyl azodicarboxylate; DMSO for dimethylsulfoxide, DIBAL or DIBAL-H for diisobutylaluminum hydride; EtOAc for ethyl acetate; HPLC for high pressure liquid chromatography; IPA for isopropyl alcohol; Ipc for isopinocamphenyl; MTBE for tert-butyl methyl ether; TBAF for tetrabutylammonium fluoride; TBS for tert-butyldimethylsilyl; TBSCl for tert-butyldimethylsilyl chloride; THF for tetrahydrofuran; Tf for —S(O)$_2$CF$_3$; TLC for thin layer chromatography; and TMS for trimethylsilyl.

The present invention will be better understood in connection with the following synthetic Schemes.

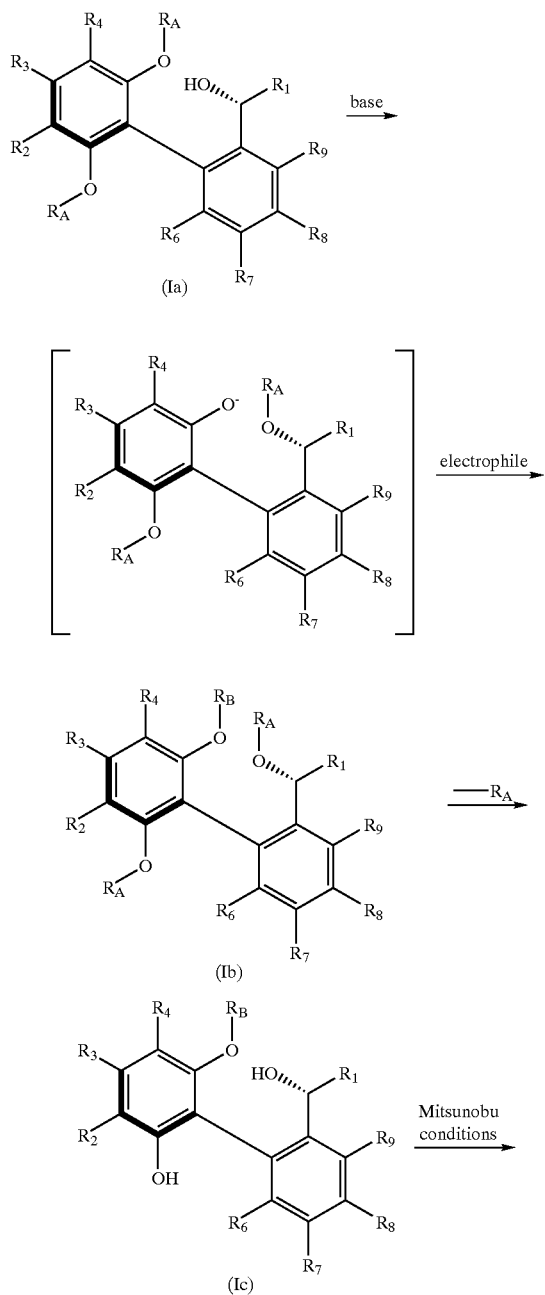

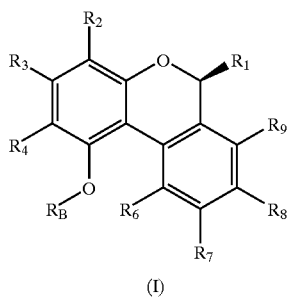

Scheme 1 describes the general applicability of the present invention to preparing compounds of general formula (I). Compounds of general formula (Ia), wherein base, electrophile, $R_B$, $R_1$, $R_2$, $R_3$, $R_4$, $R_6$, $R_7$, $R_8$ and $R_9$ are as defined herein and $R_A$ is a hydroxy protecting group, as defined herein, wherein a preferred hydroxy protecting group is tert-butyldimethylsilyl, can be treated with a base that is sufficiently basic enough to remove a proton from a secondary alcohol, a preferred base is potassium tert-butoxide, in a solvent such as tetrahydrofuran to provide an intermediate phenolic anion. The base removes the proton from the secondary alcohol facilitating migration of the hydroxy protecting group, $R_A$, spacially nearest to the alkoxide resulting in the generation of a phenolic anion which can be treated with any electrophile, as defined herein, to provide an atropisomer of general formula (Ib). The two protecting groups, $R_A$, can then be removed under standard conditions depending on $R_A$ to provide compounds of general formula (Ic). The phenolic oxygen, in compounds of general formula (Ic), is spacially orientated for nucleophilic backside attack on the carbon atom attached to the hydroxy group. This spacial arrangement in the presence of an azo and a phosphine reagent, as defined herein, in a solvent such as tetrahydrofuran facilitates an intramolecular displacement reaction providing compounds of general formula (I).

As would be understood by one skilled in the art, the opposite enantiomer of compounds of general formula (Ia) will provide the opposite enantiomer of compounds of formula (I).

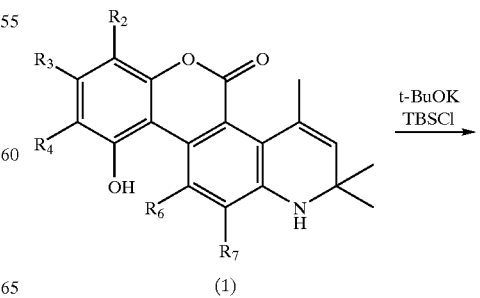

-continued

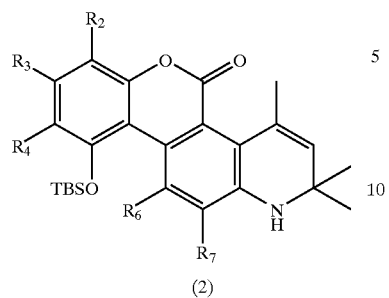

(2)

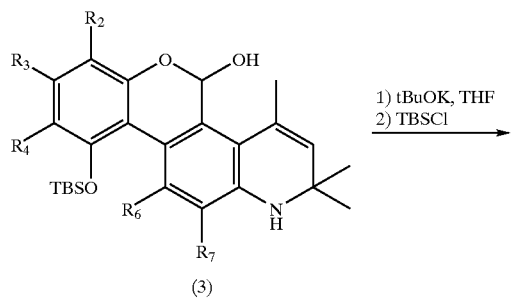

(3)

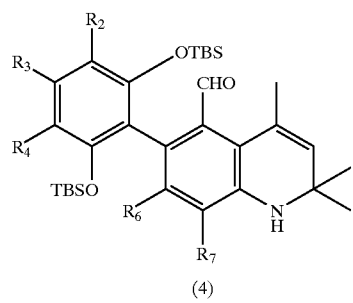

(4)

(4) + R₁—X $\xrightarrow[\text{MTBE}]{\text{(-) (Ipc)}_2\text{BCl}}$ (5)

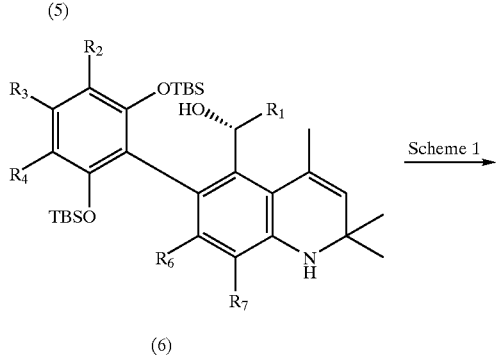

(6)

-continued

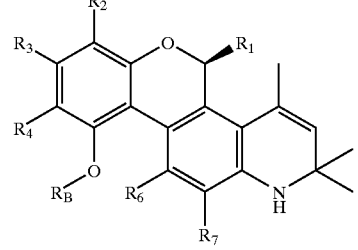

(7)

Compounds of general formula (7), wherein $R_B$, $R_1$, $R_2$, $R_3$, $R_4$, $R_6$ and $R_7$ are as defined in formula (I), can be prepared as described in Scheme 2. 1,2-Dihydro-5H-chromeno[3,4-f]quinolin-5-ones of general formula (1), prepared as described in International Publication Number WO 99/41256 and which is incorporated by reference herein, can be treated with a base such as potassium tert-butoxide and a hydroxy protecting reagent such as tert-butyldimethylsilyl chloride to provide lactones of general formula (2). Lactones of general formula (2) can be treated with a reducing agent such as diisobutylaluminum hydride in toluene at −78° C. to provide lactols of general formula (3). Lactols of general formula (3) can be treated with a base such as potassium tert-butoxide and then treated with any electrophile such as tert-butyldimethylsilyl chloride to provide bis(silyl) aldehydes of general formula (4). Bis(silyl) aldehydes of general formula (4) can be treated with a chiral chelating agent such as (−) (Ipc)₂BCl and a compound of general formula (5) wherein X is MgBr, Li or TMS in a solvent such as tert-butyl methyl ether to provide chiral alcohols of general formula (6). Chiral alcohols of general formula (6) can be processed as described in Scheme 1 or the Examples contained herein to provide compounds of general formula (7).

As would be understood by one skilled in the art, treating bis(silyl) aldehydes of general formula (4) with (+) (Ipc)₂BCl and a compound of general formula (5) will provide the opposite enantiomer of compounds of general formula (6) and processing the opposite enantiomer of compounds of general formula (6) as described in Scheme 1 will provide the opposite enantiomer of compounds of general formula (7).

Scheme 3

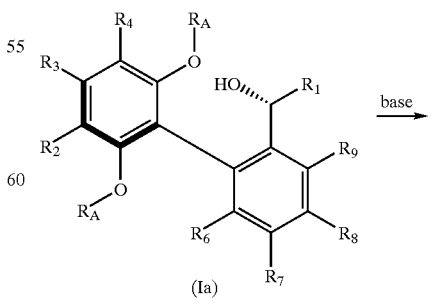

(Ia)

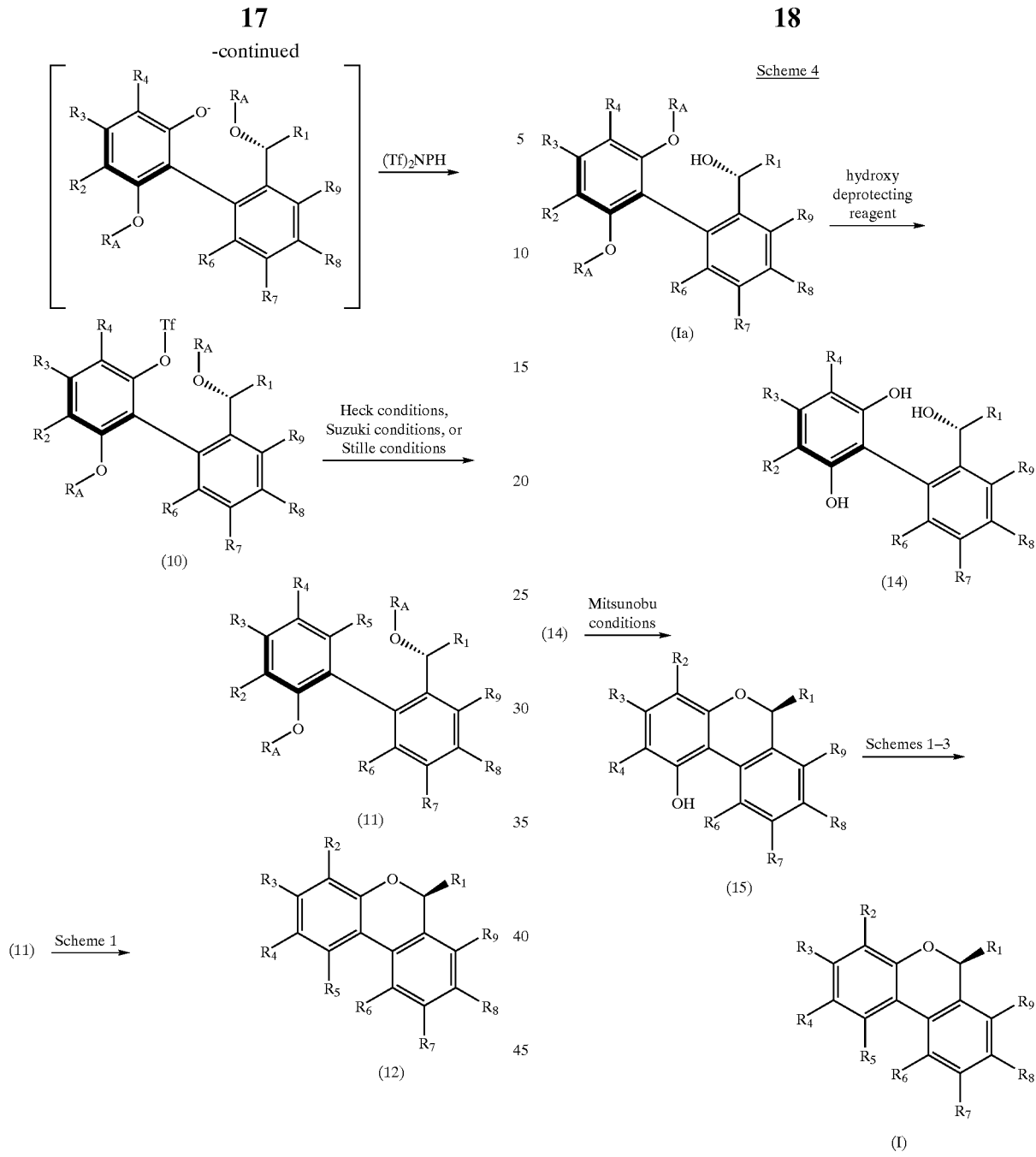

Compounds of general formula (12), wherein $R_1$, $R_2$, $R_3$, $R_4$, $R_6$, $R_7$, $R_8$ and $R_9$ are as defined in formula (I) and $R_5$ is selected from alkenyl, alkyl, alkynyl, aryl and heterocycle, can be prepared as described in Scheme 3. Compounds of general formula (Ia) can be treated with a base and then an electrophile wherein the electrophile is trifluoro-N-phenyl-N-[(trifluoromethyl)sulfonyl]methanesulfonamide or trifluoromethanesulfonic anhydride as described in Scheme 1 or the Examples contained herein to provide triflates of general formula (10). Triflates of general formula (10) can be treated under Heck, Suzuki or Stille conditions, which are well known to those of skill in the art, to provide compounds of general formula (11). Compounds of general formula (11) can be processed as described Scheme 1 or the Examples contained herein to provide compounds of general formula (12).

Alternatively, Compounds of general formula (I), wherein electrophile, $R_A$, $R_1$, $R_2$, $R_3$, $R_4$, $R_5$, $R_6$, $R_7$, $R_8$ and $R_9$ are as defined herein, can be prepared as described in Scheme 4. Compounds of general formula (Ia) can be treated with a hydroxy deprotecting reagent such as tetrabutylammonium fluoride, when $R_A$ is selected from (alkyl)(diaryl)silyl, (trialkyl)silyl, (triaryl)silyl or (triarylalkyl)silyl wherein tert-butyldimethylsilyl preferred, to provide triols of general formula (14). Triols of general formula (14) can be treated under Mitsunobu conditions as described in Scheme 1 to provide compounds of general formula (15). Compounds of general formula (15) can be processed as described in Schemes 1–3 to provide compounds of general formula (I).

The present invention is now described by the following Examples in connection with particularly preferred embodiments of Schemes 1–4. The following Examples are not intended to limit the scope the present invention. The present invention covers all alternatives, modifications and equivalents included in the appended claims. Thus, the following Examples illustrate a preferred practice of the invention, it being understood that the Examples are for the purposes of illustration of certain preferred embodiments and are presented to provide what is believed to be the most useful and readily understood description of its procedures and conceptual aspects.

EXAMPLE 1

10-{[tert-butyl(dimethyl)silyl]oxyl-}-2,2,4-trimethyl-1,2-dihydro-5H-chromeno[3,4-f]quinolin-5-one 10-hydroxy-2,2,4-trimethyl-1,2-dihydro-5H-chromeno[3,4-f]quinolin-5-one (HCl salt) (131.6 g), prepared as described in WO99/41256, in THF (2.6L) in a 5L 4-necked flask fitted with $N_2$ inlet, temperature probe and overhead stirrer was treated with t-BuOK in approximately 20 g portions over 15 minutes (103.4 g total) at 0° C. under a $N_2$ atmosphere. The cooled reaction mixture was stirred for 30 minutes. The mixture was treated with TBSCl in approximately 20 g portions over 15 minutes. The reaction was monitored by TLC, EtOAc:heptane (2:3), and/or HPLC, Zorbax Rx-C8 4.6 mm×25 cm column; mobile phase 90% $H_2O$ (0.1% $H_3PO_4$): 10% $CH_3CN$ (0.1% $H_3PO_4$) to 30:70 over 15 minutes, then to 10:90 over 20 minutes before ramping back to 10:90 over 2 minutes; 45 minute run; flow rate of 1 mL/minute; UV detection at 225 nm. Retention times: starting material—17.6 minutes; product—29.9 minutes, until starting material was consumed, about 30 minutes. The reaction mixture was quenched with 50% $NH_4Cl$ solution (1L) and extracted with EtOAc (1L). The organic layer was washed with brine (500 mL) before concentrating to a crude solid (180.8 g). The crude solid was slurried in $CH_3CN$ (900 mL) with heating until an even suspension was obtained. The suspension was then cooled to approximately 0° C., filtered and washed with cold $CH_3CN$. The wet cake was dried at 40° C. in a vacuum oven to yield 82.2 g of the title compound as a yellow solid. The mother liquors were concentrated to a solid (69 g) and re-slurried in $CH_3CN$ (250 mL). A second crop was collected and dried to yield an additional 11.8 g (81% combined yield). A small sample was crystallized from $CH_3CN$. Anal. calcd for $C_{25}H_{31}NO_3Si$: C, 71.22; H, 7.41; N, 3.32. Found: C, 68.38; H, 7.45; N, 3.16; $^1H$ NMR ($CDCl_3$) δ0.32 (6H, s), 1.05 (9H, s), 1.33 (6H, s), 2.12 (3H, s), 4.26 (1H, br), 6.75 (1H, d), 6.94~6.97 (2H, m), 7.17 (1H, t), 8.75 (1H, d); $^{13}C$ NMR ($CDCl_3$)δ−3.9, 18.4, 21.2, 25.9, 28.3, 50.4, 77.2, 110.1, 111.3, 115.4, 118.2, 120.0, 124.2, 126.9, 126.9, 127.3, 131.7, 132.0, 144.9, 151.9, 153.2, 160.1 with 3 peaks overlapping; HRMS-FAB: calcd m/z 422.2151, found 422.2137.

EXAMPLE 2

10-{[tert-butyl(dimethyl)silyl]oxy}-2,2,4-trimethyl-2,5-dihydro-1H-chromeno[3,4-f]quinolin-5-ol The product from Example 1 (37.1 g) in toluene (1.8L) under $N_2$ in a 3L 3-necked flask equipped with an overhead mechanical stirrer, addition funnel, and temperature probe was treated with diisobutylaluminum hydride in heptane (132 mL) dropwise at −78° C. over 40 minutes. After complete addition, the reaction mixture was stirred at −78° C. and monitored by HPLC, Zorbax Rx-C8 4.6 mm×25 cm column; mobile phase 90% $H_2O$ (0.1% $H_3PO_4$):10% $CH_3CN$ (0.1% $H_3PO_4$) to 30:70 over 15 minutes, then to 10:90 over 20 minutes before ramping back to 10:90 over 2 minutes; 45 minute run; flow rate of 1 mL/minute; UV detection at 225 nm. Retention times: starting material—29.9 minutes; product—20.4 minutes, and/or TLC, EtOAc:heptane (2:3), until starting material was consumed, about 1 hour. Ethyl acetate (500 mL) was added to quench any excess DIBAL, cooling was removed and saturated Rochelle's salt solution (1L) was added. The quenched mixture warmed to room temperature with stirring. The stirring was continued until layers clearly separated. The organic layer was washed with brine (500 mL) before concentrating to a solid. The isolated solid was dried at 40° C. in a vacuum oven to yield 41.2 g of the title compound as a tan solid which was used in the next step without further purification. A small reference sample was crystallized from $CH_3CN$. Anal. calcd for $C_{25}H_{33}NO_3Si$: C, 70.88; H, 7.85; N, 3.31. Found: C, 70.60; H, 7.84; N, 3.22; $^1H$ NMR [$(CD_3)_2SO$] δ0.10 (3H, s), 0.97 (9H, s), 1.08 (3H, s), 1.26 (3H, s), 2.24 (3H, s), 5.41 (1H, br), 6.07 (1H, br),6.55~6.61 (4H, m), 6.91(1H, d), 6.98 (1H, t), 7.99 (1H, d); $^{13}C$ NMR [$(CD_3)_2SO$] δ−4.5, −4.2, 18.0,22.8, 25.8, 25.8, 28.2, 30.1, 49.7, 89.9, 111.2, 113.5, 113.7, 115.7, 116.4, 116.9, 126.2, 127.2, 128.2, 130.2, 132.4, 145.3, 151.0, 151.8 with 2 peaks overlapping; HRMS-FAB: calcd m/z 423.2230, found 423.2232.

EXAMPLE 3

6-(2,6-bis {[tert-butyl(dimethyl)silyl]oxy}phenyl)-2,2,4-trimethyl-1,2-dihydroguinoline-5-carbaldehyde The product from Example 2 (40.6 g) in THF (800 mL) in a 3L 3-necked flask fitted with $N_2$ inlet, temperature probe and overhead stirrer was treated with t-BuOK in approximately 10 g portions over 5 minutes (32.3 g total) at 0° C. under $N_2$. After complete addition, the mixture was stirred for 30 minutes at 0° C. and then treated with TBSCl in approximately 10 g portions over 5 minutes (31.8 g total). The reaction was monitored by TLC, EtOAc:heptane (2:3), and/or HPLC, Zorbax Rx-C8 4.6 mm×25 cm column; mobile phase 90% $H_2$(0.1% $H_3PO_4$): 10% $CH_3CN$ (0.1% $H_3PO_4$) to 30:70 over 15 minutes, then to 10:90 over 20 minutes, held at 10:90 for 20 minutes before ramping back to 10:90 over 2 minutes; 65 minutes run; flow rate of 1.5 mL/minute; UV detection at 225 nm. Retention times: starting material-20.4 minutes; product-34.9 minutes, until starting material was consumed, about 30 minutes. The reaction mixture was quenched with 50% $NH_4Cl$ solution (500 mL) and extracted with EtOAc (500 mL). The organic layer was washed with brine (500 mL) before concentrating to crude solid (57.0 g). The crude solid was slurried in methanol (230 mL) with heating until an even suspension. The suspension was then cooled to approximately 0° C., filtered and washed with cold methanol. The wet cake was dried in a vacuum oven at 40° C. to yield 36.1 g of the title compound as a white solid. A small reference sample was crystallized from methanol. Anal. Calcd for $C_{31}H_{47}NO_3Si_2$: C, 69.22; H, 8.81; N, 2.60. Found: C, 69.00; H, 9.10; N, 2.60; $^1H$ NMR ($CDCl_3$) δ0.01 (12H, s), 0.71 (18H, s), 1.28 (6H, s), 1.87 (3H, s), 3.94 (1H, br), 5.51 (1H, br), 6.52 (2H, b), 6.73 (1H, d), 6.88 (1H, d), 7.06 (1H, t), 10.07 (1H, s); $^3C$ NMR ($CDCl_3$) δ−4.7, 17.7, 22.4, 25.2,28.3, 50.3, 112.7, 117.4, 121.8, 123.1, 127.7, 128.3, 130.4, 131.9, 132.2, 134.5, 144.6, 154.5, 196.1 with 12 peaks overlapping; HRMS-FAB: calcd m/z 538.3173, found 538.3151.

EXAMPLE 4

(1R)-1-[6-(2,6-bis{[tert-butyl(dimethyl)silyl] oxy}phenyl)-2,2,4-trimethyl-1,2-dihydroquinolin-5-yl]but-3-en-1-ol (+) Chlorodiisopinocamphenylborane(52.5 g) in MTBE (1.8L) under $N_2$ in a 5L 4-necked flask fitted with $N_2$ inlet, addition funnel, temperature probe and overhead stirrer was treated with allylmagnesium bromide dropwise over 40–50 minutes (147 mL) at −78° C. After complete addition, the mixture was stirred for 2 hours (−78° C.) and then the mixture was treated with the product from Example 3 (44.0 g dissolved in 400 mL MTBE) dropwise while maintaining the reaction temperature −78° C. The reaction was monitored by TLC, EtOAc:heptane (2:3), and/or HPLC, Zorbax Rx-C8 4.6 mm×25 cm column; mobile phase 90% $H_2O$ (0.1% $H_3PO_4$): 10% $CH_3CN$ (0.1% $H_3PO_4$) to 30:70 over 15 minutes, then to 10:90 over 20 minutes, held at 10:90 for 20 minutes before ramping back to 10:90 over 2 minutes; 65 minute run; flow rate of 1.5 mL/minute; UV detection at 225 nm. Retention times: starting material—34.9 minutes; product—34.3 minutes, until starting material was consumed, about 30–60 minutes. The reaction mixture was quenched with 5% $NaHCO_3$ solution (1L) and extracted with hexanes (1L). The organic layer was washed with brine (500 mL) before concentrated to a tan oil (102 g). After sitting at room temperature open to the environment for 72 hours, the oil partially solidified. The crude oil/solid was slurried in hexanes (2–300 mL), cooled under vacuum (0° C.) and filtered. The precipitate was washed with hexanes, dried in a vacuum oven at 40° C. to yield 10.5 g. Additional precipitate was obtained from the cooled mother liquors to yield an additional 36.3 g (94% potency yield) of the title compound as a white solid. The isolated product can be triturated with methanol to improve color and purity. A small reference sample was crystallized from methanol. Anal. Calcd for $C_{34}H_{53}NO_3Si_2$: C, 70.41; H, 9.21; N, 2.42. Found: C, 69.13; H, 8.76; N, 2.30; $^1H$ NMR [$(CD_3)_2SO$] δ−0.09 (3H, s), 0.04 (3H, s), 0.08 (3H, s), 0.10 (3H, s), 0.68 (9H, s), 0.68 (9H, s), 1.09 (3H, s), 1.15 (3H, s), 2.10 (1H, m), 2.15 (3H, s), 2.21 (1H, m), 4.01 (1H, d), 4.62(1H, m), 4.72~4.80 (2H, m), 5.40 (1H, br), 5.62 (1H, m), 5.84 (1H, br), 6.51 (1H, d), 6.57~6.59 (3H, m), 7.13 (1H, t); $^{13}C$ NMR [$(CD_3)_2SO$] δ−5.0, −4.8, −4.7, −4.6, 17.4, 17.5, 23.2,25.1, 25.2, 26.6, 27.5, 40.1, 48.8, 17.7, 112.2, 112.6, 113.1, 115.3, 122.4, 122.9, 127.1, 128.3, 130.3, 131.8, 132.0, 137.6, 138.4, 145.9, 153.5, 154.3; ESI-MS: m/z 580 (M+H)$^+$, HRMS-FAB: calcd m/z 579.3564, found 579.3568.

EXAMPLE 5

5-((1R)-1-{[tert-butyl(dimethyl)silyl]oxy}but-3-enyl)-6-(2-{[tert-butyl(dimethyl)silyl]oxy}-6-methoxyphenyl)-2,2,4-trimethyl-1,2-dihydroquinoline A 1L three-necked round bottom flask was charged with the product from Example 4 (25 g) in THF (1.37L) and treated with a 1M solution of t-BuOK (58 ml) dropwise over 20 minutes at 0° C. The reaction was monitored by TLC, EtOAc:hexanes (2:3), and/or HPLC, Zorbax SB-CS; Flow rate: 1.5 ml/minute; 50:50 to 90:10 acetonitrile:water (0.1% $H_3PO_4$) over 10 minutes, then 90:10 to 95:05 acetonitrile:water (0.1% $H_3PO_4$) over 25 minutes; UV detection: 225 nm. Retention time for starting material 18.6 minutes; Retention time for the silyl group migration intermediate: 19.6 minutes. After the completion of the reaction was determined, iodomethane (6.4 ml) was added to the reaction mixture all at once. The ice-bath was removed and the mixture was allowed to warm to room temperature and stirred for two hours. Completion of the reaction was monitored with HPLC. HPLC conditions: Zorbax SB-CS; Flow rate: 1.5 ml/minute; 50:50 to 90:10 acetonitrile:water (0.1% $H_3PO_4$) over 10 minutes, then 90:10 to 95:05 acetonitrile:water (0.1% $H_3PO_4$) over 25 minutes; UV detection: 225 nm. Retention time for the silyl group migration intermediate: 19.6 minutes; Retention time for the methylation product: 20.6 minutes. The reaction mixture was poured into saturated $NH_4Cl$ solution (500 ml) and stirred briefly. The organic layer was separated, washed with brine (500 ml), dried over $NaSO_4$, and concentrated to give an orange oil. Heptane (250 ml) was added to the oil residue to dissolve the crude product. The solution was extracted with $CH_3CN$ (2×15 ml) and was treated with charcoal and concentrated to dryness to give 26.6 g crude product as an oil residue. A small reference sample of the product was obtained by column chromatography purification eluting with heptane:ethyl acetate (95:2). $^1H$ NMR [$(CD_3)_2SO$] δ−0.22 (3H, s), −0.19 (3H, s), −0.17 (3H, s), 0.01 (3H, s), 0.78 (9H, s), 0.80 (9H, s), 1.06 (3H, s), 1.22 (3H, s), 2.23 (3H, s),2.32 (1H, br), 2.54 (1H, br), 3.61 (3H, s), 4.66 (2H, m), 4.77 (11H, d), 5.33 (2H, s), 5.77 (1H, s), 6.46 (1H, br), 6.55 (2H, m), 6.68 (1H, d), 7.19 (1H, t); $^{13}C$ NMR [$(CD_3)_2SO$] δ−5.5, −4.6, −4.5, −4.3, 17.8, 17.9, 25.8, 29.4, 41.4, 48.6, 55.1, 74.3, 104.6, 112.9, 115.8, 121.2, 122.5, 123.1, 127.1, 128.3, 130.1, 131.3, 137.5, 140.0, 146.4, 153.7, 158.6; ESI-MS: m/z 594 (M+H)$^+$, HRMS-FAB: calcd m/z 593.3721, found 593.3699.

EXAMPLE 6

2-{5-[(1R)-1-hydroxybut-3-enyl]-2,2,4-trimethyl-1,2-dihydroquinolin-6-yl}-3-methoxyphenol The product from Example 5 (26.0 g) in THF (250 mL) was purged with nitrogen for 10 minutes at room temperature and then treated with a 1.0M TBAF solution all at once, a dark purple solution formed. The reaction mixture was stirred at room temperature overnight. The completion of the reaction was monitored with both HPLC and TLC. TLC: 40% EtOAc in Hexane, starting material Rf: 6.0, the desilylation product Rf: 3.0. HPLC conditions: Zorbax SB-CS; flow rate: 1.0 ml/minutes 90:10 to 30:70 acetonitrile:water (0.1% $H_3PO_4$) over 15 minutes, then 30:70 to 10:90 acetonitrile:water (0.1% $H_3PO_4$) over 20 minutes; UV detection at 225 nm. The reaction mixture was poured into a solution of saturated $NH_4Cl$ (250 ml), stirred briefly and added MTBE (150 ml). The mixture was stirred for 5 minutes and the organic layer was separated. The organics were washed with brine (200 ml), dried over $Na_2SO_4$ and concentrated to dryness to give light yellow solid. The solid was then suspended in IPA (20 ml)/heptane (250 ml) at room temperature for two hours at room temperature, then cooled to 0° C. The suspension was filtered to give 13.6 g of the title compound as a light yellow solid which was used in the next step without further purification. $^1H$ NMR [$(CD_3)_2SO$] δ1.13 (3H, s), 1.18 (3H,s), 2.19 (3H, s), 2.27 (2H, m), 3.61 (3H, s), 4.14(1H, d), 4.65 (1H, m), 4.75 (2H, d), 5.38 (1H, s), 5.48 (1H, m), 5.83 (1H, s), 6.49~6.55 (4H, m), 7.09 (1H, t), 9.02 (1H, s); $^{13}C$ NMR [$(CD_3)_2SO$]δ24.2, 27.6, 28.3, 40.1, 48.8, 55.4, 71.7, 102.5, 108.8, 113.2, 115.3, 119.3, 122.2, 122.7, 128.2, 130.4, 131.3, 131.6, 137.3, 139.2, 145.6, 155.8, 158.0; ESI-MS: m/z 366 (M+H)$^+$; HRMS-FAB: calcd m/z 365.1991, found 365.1989.

EXAMPLE 7

(5S)-5-allyl-10-methoxy-2,2,4-trimethyl-2,5-dihydro-1H-chromeno[3,4-f]quinoline

The product from Example 6 (10.0 g) and triphenylphosphine (17.97 g) in THF was stirred briefly at room temperature to dissolve the solids and then cooled to −2° C. The cooled solution was treated with DIAD (12.7 ml) in THF (135 ml) dropwise over about 1.5 hours while maintaining the temperature below 0° C. The reaction mixture was stirred at 0° C. for two hours and then was slowly warmed to room temperature over a two hour period. The reaction was monitored with HPLC, in case of incomplete reaction, more reagents could be added to the reaction mixture following the same sequence, i.e. addition of triphenylphosphine first followed by DIAD solution. HPLC conditions: Zorbax SB-CS; flow rate: 1.0 ml/minutes 90:10 to 30:70 acetonitrile: water (0.1% $H_3PO_4$) over 15 minutes, then 30:70 to 10:90 acetonitrile:water (0.1% $H_3PO_4$) over 20 minutes; UV detection at 225 nm. Retention time: starting material diol: 15.5 minutes, the product allyl compound: 25.5 minutes, the by-product triphenylphosphine oxide. The solvent was concentrated under vacuum to about 300 ml, heptane was added, and the mixture was cooled in the refrigerator overnight. The solid was filtered, the filtrate was further concentrated upon cooling when vacuum was applied. More solid was precipitated out. When the total volume of the filtrate was about 400 ml, the solid was filtered again. When the filtrate contained very small amounts of triphenylphosphine oxide, the filtrate was concentrated to an oil. The oil was purified by column chromatography with 5% EtOAc/hexane to give 6.05 g (85% ee, which was determined by chiral HPLC using a Chiralcel OJ 4.6×250 mm column with hexane/ethanol as eluting solvents) of the title compound as an off-white foam. The % ee was further improved by crystallization with IPA to 98.5% with 75% recovery. Anal. Calcd for $C_{23}H_{25}NO_2$: C, 79.51; H, 7.25 and N, 4.03; Found: C, 79.26; H, 7.12 and N, 3.80; $^1H$ NMR [$(CD_3)_2SO$] δ1.16 (3H, s) 1.17 (3H, s), 2.18 (3H, s), 2.22 (1H, m), 3.85 (3H, s), 5.01 (2H, m), 5.44 (1H, br s), 5.77 (1H, dd), 5.82 (1H, m), 6.10 (1H, br s), 6.52 (1H, d), 6.60 (1H, d), 6.70 (1H, d), 7.06 (1H, t) and 7.96 (1H, d); $^{13}C$ NMR [$(CD_3)_2SO$] δ23.8, 28.8, 28.9, 36.5, 49.7, 55.6, 73.4, 105.6, 110.5, 113.4, 116.1, 116.4, 127.3, 117.3, 127.3, 127.7, 132.2, 133.8, 134.5, 145.8, 151.1, 156.4. APCI-MS: m/z 348 (M+H)$^+$.

EXAMPLE 8

2-{-[(1R)-1-hydroxybut-3-enyl]-2,2,4-trimethyl-1,2-dihydroquinolin-6-yl}benzene-1,3-diol The product from Example 4 (1.0 g, 1.7 mmol) in THF (15 mL) and acetic acid (0.1 mL) was purged with $N_2$ for 10 minutes at room temperature and then treated with a 1.0 M solution of TBAF in THF (7.6 mL). The reaction mixture was stirred at room temperature overnight under $N_2$. HPLC indicated that the de-silylation was complete. The reaction mixture was poured into a solution of saturated $NH_4Cl$ (30 mL) and stirred briefly before MTBE (30 mL) was added. After stirring for 5 minutes, the organic layer was separated, washed with brine, dried over $Na_2SO_4$ and concentrated to dryness to give light yellow solid. The solid was then recrystallized with EtOAc/heptane to give the title compound (520 mg) as an off-white solid. $^1H$ NMR [$(CD_3)_2SO$] δ1.10(3H, s), 1.22(3H, s), 2.17(3H, s), 2.23 (2H, m), 4.76~4.80 (3H, m), 5.12 (1H, d), 5.40 (1H, br), 5.52(1H, m), 5.88 (1H, br), 6.43 (1H, dd), 6.53 (2H, m), 6.93 (1H, t), 8.92 (1H, s), 9.09 (1H, s); $^{13}C$ NMR [$(CD_3)_2SO$]δ23.3, 27.2, 28.6, 39.8, 48.9, 71.2, 107.1, 107.4, 113.0, 115.3, 119.3, 122.2, 122.5, 127.6, 129.6, 131.6, 132.2, 136.8, 138.3, 145.0, 154.8, 155.9; ESI-MS: m/z 352 (M+H)$^+$; HRMS-FAB: calcd 351.1834, found 351.1829.

EXAMPLE 9

(5S)-5-allyl-2,2,4-trimethyl-2,5-dihydro-1H-chromeno[3,4-f]quinolin-10-ol

The product of Example 8 (0.8 g, 2 mmol) and triphenylphosphine (1.4 g, 5 mmol) in THF (50 mL) were treated with DIAD (1.0 mL, 5 mmol) in THF (1 mL) dropwise at 0° C. After 30 minutes, the cooling bath was removed and the mixture was allowed to warm to room temperature with stirring. After 1 hour, reaction was complete by HPLC. Heptane was added and precipitated triphenylphosphine oxide was then filtered off. The filtrate was concentrated and the residue purified by column chromatography with silica gel eluting with EtOAc/heptane to give the title compound as a solid (157 mg).

EXAMPLE 10

(5S)-5-allyl-10-methoxy-2,2,4-trimethyl-2,5-dihydro-1H-chromeno[3,4-f]quinoline

The product from Example 9 (157 mg) in THF (10 ml) was treated with a 1.0 M solution of tBuOK (1.0 ml) at 0° C. and then treated with iodomethane (0.1 ml). After stirring at room temperature for 2 hours, the mixture was poured into a solution of saturated $NH_4Cl$ (15 mL) and stirred briefly before MTBE (15 mL) was added. After stirring for 5 minutes, the organic layer was separated, washed with brine, dried over $Na_2SO_4$ and concentrated to dryness. The residue was purified by column chromatography to give the title compound (134 mg). Anal. calcd for $C_{23}H_{25}NO_2$: C, 79.51; H, 7.25 and N, 4.03; Found: C, 79.26; H, 7.12 and N, 3.80; $^1H$ NMR [$(CD_3)_2SO$] δ1.16 (3H, s) 1.17 (3H, s), 2.18 (3H, s), 2.22 (1H, m), 2.46 (1H, m), 3.85 (3H, s), 5.01 (2H, m), 5.44 (1H, br s), 5.77 (1H, dd), 5.82 (1H, M), 6.10 (1H, br s), 6.52 (1H, d), 6.60 (1H, d), 6.70 (1H, d), 7.06 (1H, t) and 7.96 (1H, d); $^{13}C$NMR [$(CD_3)_2SO$] δ23.8, 28.8, 28.9, 36.5, 49.7, 55.6, 73.4, 105.6, 110.5, 113.4, 113.4, 116.1, 116.4, 127.3, 117.3, 127.3, 127.7, 132.2,133.8, 134.5, 145.8, 151.1, 156.4; APCI-MS: m/z 348 (M+H)$^+$.

EXAMPLE 11

3-{[tert-butyl(dimethyl)silyl]oxy}-2-[5-((1R)-1-{[tert-butyl(dimethyl)silyl]oxy}but-3-enyl 2,2,4-Trimethyl-1,2-Dihydroquinolin-6-Yl]Phenyl Trifluoromethanesulfonate The product of Example 4 (1.74 g, 3.0 mmol) in THF (150 mL) at 0° C. was treated with a 1.0M solution of t-BuOK in THF (3.9 mL) dropwise while keeping the temperature below at 0° C. After migration was complete (as determined by HPLC), the mixture was treated with trifluoro-N-phenyl-N-[(trifluoromethyl)sulfonyl]methanesulfonamide (1.6 g, 4.5 mmol) in one portion. The cooling bath was removed and the reaction mixture was allowed to warm to room temperature and stir for 6 hours. The reaction mixture was then poured into saturated $NH_4Cl$ solution (150 mL), stirred briefly, and MTBE (80 mL) was added. The organic layer was separated, washed with brine, dried over $Na_2SO_4$, and concentrated to an orange oil. The orange oil was dissolved in heptane (50 mL) and extracted with $CH_3CN$ (5 mL, 2×) to remove color and impurities. The heptane layers were concentrated to dryness to give the title compound (1.8 g) as an oil. A small reference sample of the product was obtained as a colorless oil by column chromatography purification eluting with heptane:ethyl acetate (95:2). $^1H$ NMR ($C_5D_5N$) δ0.11 (3H, s), 0.13 (3H, s), 0.14 (3H, s), 0.23 (3H, s), 0.89 (9H, s), 0.99 (9H, s), 1.34 (3H, s), 1.37 (3H, s), 2.41 (3H, s), 2.82 (2H, m), 5.02~5.09 (2H, m), 5.61 (H, m), 6.92 (1H, d), 7.02 (1H, m), 7.10 (1H, d), 7.18 (1H, d), 7.21 (NH, 7.39 (1H, m); $^{13}C$ NMR [$(CD_3)$2SO] δ−4.2, −4.0, −3.6, 18.3, 18.5, 25.0, 25.9, 26.5, 28.1, 28.4, 43.2, 49.9, 74.3, 113.2, 114.2, 116.1, 119.3, 120.2, 128.8, 130.2, 132.5, 133.3, 137.4, 140.2, 147.3, 156.0; MS (APCI) m/z: 713 (M+H)$^+$; HRMS-FAB: calcd m/z 712.3133, found 712.3143.

What is claimed is:

1. A process for the preparation of a compound having formula (I)

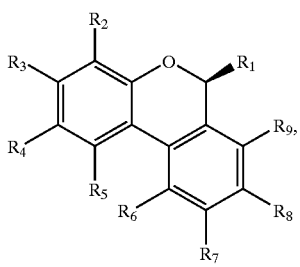

wherein
- $R_1$ is selected from the group consisting of alkenyl, alkyl, alkynyl and aryl;
- $R_2$, $R_3$ and $R_4$ are each independently selected from the group consisting of hydrogen, alkoxy, alkenyl, alkyl, alkynyl, aryl and halogen; or
- $R_2$ and $R_3$ or $R_3$ and $R_4$ together with the carbon atoms to which they are attached, together form a ring wherein the ring is selected from the group consisting of aryl, cycloalkyl and heterocycle;
- $R_5$ is selected from the group consisting of hydrogen, alkenyl, alkenyloxy, alkoxy, alkoxycarbonyloxy, alkoxysulfonyloxy, alkyl, alkylcarbonyloxy, alkylsulfonyloxy, alkynyl, alkynyloxy, aryl, arylalkoxy, arylalkoxycarbonyloxy, aryloxy, arylsulfonyloxy, haloalkoxy, haloalkylcarbonyloxy, haloalkylsulfonyloxy, halogen, heterocycle and $(NR_CR_D)$carbonyloxy wherein $R_C$ and $R_D$ are each independently selected from the group consisting of hydrogen and alkyl; and
- $R_6$, $R_7$, $R_8$ and $R_9$ are each independently selected from the group consisting of hydrogen, alkoxy, alkenyl, alkyl, alkynyl, aryl and halogen; or
- $R_6$ and $R_7$ or $R_7$ and $R_8$ or $R_8$ and $R_9$ together with the carbon atoms to which they are attached, together form a ring wherein the ring is selected from the group consisting of aryl, cycloalkyl and heterocycle;

wherein said process comprises the steps of:
(a) treating a compound of formula (Ia) with a base in a first solvent

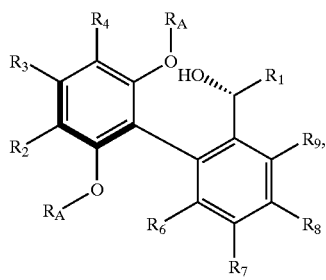

wherein $R_A$ is a hydroxy protecting group and $R_1$, $R_2$, $R_3$, $R_4$, $R_6$, $R_7$, $R_8$ and $R_9$ are as defined above;
(b) treating the product of step (a) with an electrophile to provide a compound of formula (Ib)

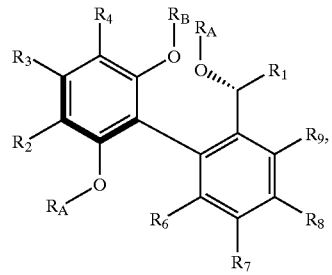

wherein $R_B$ is selected from the group consisting of alkoxycarbonyl, alkoxysulfonyl, alkenyl, alkyl, alkylcarbonyl, alkylsulfonyl, alkynyl, arylalkoxycarbonyl, arylalkyl, arylsulfonyl, haloalkyl, haloalkylcarbonyl, haloalkylsulfonyl and $(NR_CR_D)$carbonyl; and $R_A$, $R_C$, $R_D$, $R_1$, $R_2$, $R_3$, $R_4$, $R_6$, $R_7$, $R_8$ and $R_9$ are as defined above;
(c) treating the compound of formula (Ib) with a hydroxy deprotecting reagent in a second solvent to provide a compound of formula (Ic)

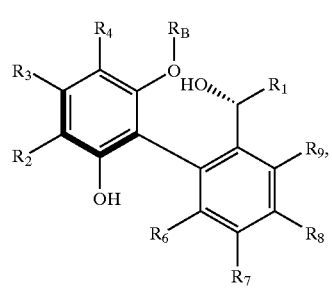

wherein $R_B$, $R_1$, $R_2$, $R_3$, $R_4$, $R_6$, $R_7$, $R_8$ and $R_9$ are as defined above; and
(d) treating the compound of formula (Ic) with an azo reagent and a phosphine reagent in a third solvent.

2. The process according to claim 1 wherein
- $R_2$, $R_3$, $R_4$, $R_6$ and $R_7$ are each hydrogen; and
- $R_8$ and $R_9$ together with the carbon atoms to which they are attached, together form a ring wherein the ring is selected from the group consisting of aryl, cycloalkyl and heterocycle.

3. The process according to claim 1 wherein
- $R_1$ is alkenyl;
- $R_2$, $R_3$, $R_4$, $R_6$ and $R_7$ are each hydrogen; and
- $R_8$ and $R_9$ together with the carbon atoms to which they are attached, together form a ring wherein the ring is heterocycle.

4. The process according to claim 1 wherein
- $R_1$ is alkenyl;
- $R_2$, $R_3$, $R_4$, $R_6$ and $R_7$ are each hydrogen; and
- $R_8$ and $R_9$ together with the carbon atoms to which they are attached, together form a ring wherein the ring is heterocycle wherein the heterocycle is 4,6,6-trimethyl-1,2,3,6-tetrahydropyridinyl.

5. The process according to claim 1 wherein
- $R_1$ is alkenyl;
- $R_2$, $R_3$, $R_4$, $R_6$ and $R_7$ are each hydrogen;
- $R_5$ is alkoxy; and $R_8$ and $R_9$ together with the carbon atoms to which they are attached, together form a ring wherein the ring is heterocycle wherein the heterocycle is 4,6,6-trimethyl-1,2,3,6-tetrahydropyridinyl.

6. The process according to claim 1 wherein the compound of formula (I) is (5S)-5-allyl-10-methoxy-2,2,4-trimethyl-2,5-dihydro-1H-chromeno[3,4-f]quinoline.

7. The process according to claim 1 wherein
$R_1$ is alkenyl;
$R_2$, $R_3$, $R_4$, $R_6$ and $R_7$ are each hydrogen;
$R_5$ is haloalkylsulfonyloxy; and
$R_8$ and $R_9$ together with the carbon atoms to which they are attached, together form a ring wherein the ring is heterocycle wherein the heterocycle is 4,6,6-trimethyl-1,2,3,6-tetrahydropyridinyl.

8. The process according to claim 1 wherein the compound of formula (I) is (5S)-5-allyl-2,2,4-trimethyl-2,5-dihydro-1H-chromeno[3,4-f]quinolin-10-yl trifluoromethanesulfonate.

9. The process according to claim 1 wherein in step (a) the hydroxy protecting group is selected from the group consisting of acetyl, trimethylsilyl, triethylsilyl, triisopropylsilyl, dimethylisopropylsilyl, diethylisopropylsilyl, tert-butyldimethylsilyl, methyldiphenylsilyl, tert-butyldiphenylsilyl, tribenzylsilyl and triphenylsilyl.

10. The process according to claim 1 wherein in step (a) the hydroxy protecting group is tert-butyldimethylsilyl.

11. The process according to claim 1 wherein in step (a) the base is selected from the group consisting of sodium methoxide, sodium ethoxide, potassium methoxide, potassium ethoxide, potassium tert-butoxide, sodium hydride, potassium hydride, lithium hydride, lithium diisopropylamide, lithium bis(trimethylsilyl)amide, potassium bis(trimethylsilyl)amide and sodium bis(trimethylsilyl)amide.

12. The process according to claim 1 wherein in step (a) the base is potassium tert-butoxide.

13. The process according to claim 1 wherein in step (b) the electrophile is selected from the group consisting of acetyl chloride, propionyl chloride, trimethylacetyl chloride, dimethylcarbamyl chloride, allyl bromide, methyltriflate, methyltosylate, dimethylsulfate, iodomethane, iodoethane, trifluoromethyl iodide, perfluoroethyl iodide, benzyl bromide, benzyl chloride, propargyl bromide, acetic anhydride, trifluoromethyl anhydride, di-tert-butyl dicarbonate, benzyl chloroformate, ethyl chloroformate, isopropyl chloroformate, methanesulfonyl chloride, para-toluenesulfonyl chloride, phenylsulfonyl chloride, trifluoro-N-phenyl-N-[(trifluoromethyl)sulfonyl]methanesulfonamide and trifluoromethanesulfonic anhydride.

14. The process according to claim 1 wherein in step (b) the electrophile is selected from the group consisting of iodomethane and trifluoro-N-phenyl-N-[(trifluoromethyl)sulfonyl]methanesulfonamide.

15. The process according to claim 1 wherein in step (c) the hydroxy deprotecting reagent is selected from the group consisting of tetrabutylammonium fluoride, potassium fluoride, hydrogen fluoride, hydrochloric acid, hydrobromic acid, acetic acid, trifluoroacetic acid, aqueous potassium hydroxide, aqueous sodium hydroxide, aqueous potassium carbonate and aqueous sodium bicarbonate.

16. The process according to claim 1 wherein in step (c) the hydroxy deprotecting reagent is tetrabutylammonium fluoride.

17. The process according to claim 1 wherein in step (d) the azo reagent is selected from the group consisting of diethyl azodicarboxylate, di-tert-butyl azodicarboxylate, diisopropyl azodicarboxylate, dimethyl azodicarboxylate and dicyclohexyl azodicarboxylate; and the phosphine reagent is selected from the group consisting of tributylphosphine, tri-tert-butylphosphine, triisobutylphosphine, triisopropylphosphine, tripropylphosphine, triethylphosphine, trimethylphosphine, tris(4-methylphenyl)phosphine, tris(4-methoxyphenyl)phosphine, tris(4-chlorophenyl)phosphine, tris(4-bromophenyl)phosphine and triphenylphosphine.

18. The process according to claim 1 wherein in step (d) the azo reagent is diisopropyl azodicarboxylate; and the phosphine reagent is triphenylphosphine.

19. The process according to claim 1 wherein
in step (a) the compound of formula (Ia) is (1R)-1-[6-(2,6-bis{[tert-butyl(dimethyl)silyl]oxy}phenyl)-2,2,4-trimethyl-1,2-dihydroquinolin-5-yl]but-3-en-1-ol; the base is potassium tert-butoxide; and the first solvent is tetrahydrofuran;

in step (b) the electrophile is iodomethane;

in step (c) the hydroxy deprotecting reagent is tetrabutylammonium fluoride; and the second solvent is tetrahydrofuran; and in step (d) the azo reagent is diisopropyl azodicarboxylate; the phosphine reagent is triphenylphosphine; and the third solvent is tetrahydrofuran.

20. The process according to claim 19 wherein
step (a) is conducted from about −5° C. to about 25° C.

21. The process of claim 20 further comprising isolating the product of step (b) by pouring step (b) into saturated ammonium chloride solution; stirring the solution; separating the aqueous phase from the organic phase; washing the organic phase with brine; drying the organic phase over sodium sulfate; concentrating the organic phase to provide an oil; dissolving the oil in heptane; extracting the heptane with acetonitrile; treating the heptane with charcoal; and concentrating the heptane.

22. The process according to claim 21 wherein step (c) is conducted between 18° C. and about 25° C. for about 12 to 36 hours.

23. The process according to claim 22 further comprising isolating the product of step (c) by pouring step (c) into a saturated solution of ammonium chloride; stirring the solution; adding tert-butyl methyl ether to the solution; stirring the solution for about 5 to 20 minutes; separating the aqueous phase from the organic phase; washing the organic phase with brine; drying the organic phase over sodium sulfate; concentrating the organic phase to provide a solid; suspending the solid in isopropanol:heptane 1:12.5 for 1 to 3 hours; cooling the isopropanol:heptane 1:12.5 to −5° C. to about 5° C.; and filtering the isopropanol:heptane 1:12.5.

24. The process according to claim 23 wherein in step (d) the product of step (c) and the triphenylphosphine are dissolved in the tetrahydrofuran at a temperature between about 18° C. and about 25° C.; the tetrahydrofuran is cooled to about −5° C. to about 15° C.; and the diisobutyl azodicarboxylate is added to the tetrahydrofuran over about 0.25 to 3 hours while maintaining the temperature of the tetrahydrofuran from about −5° C. to about 25° C.

25. The process according to claim 24 further comprising isolating the product from step(d) by concentrating the tetrahydrofuran to about ¼ to ⅓ of original volume; adding heptane to the tetrahydrofuran; cooling the tetrahydrofuran/heptane mixture to about −5° C. to about 5° C.; allowing the tetrahydrofuran/heptane mixture to stand for 12 to 24 hours; filtering the tetrahydrofuran/heptane mixture; repeating concentration, cooling and filtering until small amount of solid precipitates out of the tetrahydrofuran/heptane mixture; concentrating the tetrahydrofuran/heptane mixture to provide crude product of step (d); purifying the crude product of step (d) by flash chromatography to provide the product of step (d); and recrystallizing the product of step (d) from isopropanol.

26. A process for the preparation of a compound having formula (II)

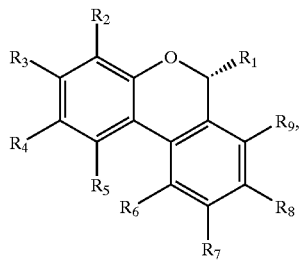
(II)

wherein
- $R_1$ is selected from selected from the group consisting of alkenyl, alkyl, alkynyl and aryl;
- $R_2$, $R_3$ and $R_4$ are each independently selected from the group consisting of hydrogen, alkoxy, alkenyl, alkyl, alkynyl and halogen; or
- $R_2$ and $R_3$ or $R_3$ and $R_4$ together with the carbon atoms to which they are attached, together form a ring wherein the ring is selected from the group consisting of aryl, cycloalkyl and heterocycle;
- $R_5$ is selected from the group consisting of hydrogen, alkenyl, alkenyloxy, alkoxy, alkoxycarbonyloxy, alkoxysulfonyloxy, alkyl, alkylcarbonyloxy, alkylsulfonyloxy, alkynyl, alkynyloxy, aryl, arylalkoxy, arylalkoxycarbonyloxy, arylsulfonyloxy, haloalkoxy, haloalkylcarbonyloxy, haloalkylsulfonyloxy, halogen, heterocycle and $(NR_CR_D)$carbonyloxy; and
- $R_6$, $R_7$, $R_8$ and $R_9$ are each independently selected from the group consisting of to hydrogen, alkoxy, alkenyl, alkyl, alkynyl and halogen; or
- $R_6$ and $R_7$ or $R_7$ and $R_8$ or $R_8$ and $R_9$ together with the carbon atoms to which they are attached, together form a ring wherein the ring is selected from the group consisting of aryl, cycloalkyl and heterocycle;

wherein said process comprises the steps of:
(a) treating a compound of formula (IIa) with a base in a first solvent

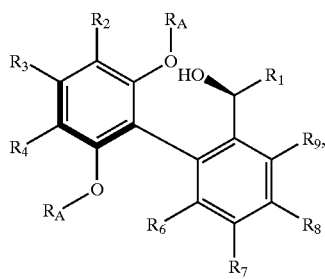
(IIa)

wherein $R_A$ is a hydroxy protecting group and $R_1$, $R_2$, $R_3$, $R_4$, $R_6$, $R_7$, $R_8$ and $R_9$ are as defined above;
(b) treating the product of step (a) with an electrophile to provide a compound of formula (IIb)

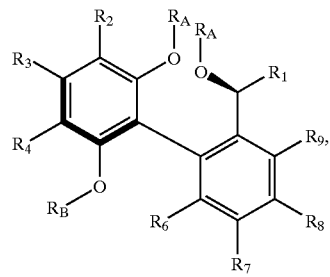
(IIb)

wherein $R_B$ is selected from the group consisting of alkoxycarbonyl, alkoxysulfonyl, alkenyl, alkyl, alkylcarbonyl, alkylsulfonyl, alkynyl, arylalkoxycarbonyl, arylalkyl, arylsulfonyl, haloalkyl, haloalkylcarbonyl, haloalkylsulfonyl and $(NR_CR_D)$carbonyl wherein $R_C$ and $R_D$ are selected from the group consisting of hydrogen and alkyl; and $R_A$, $R_1$, $R_2$, $R_3$, $R_4$, $R_6$, $R_7$, $R_8$ and $R_9$ are as defined above;

(c) treating the compound of formula (IIb) with a hydroxy deprotecting reagent in a second solvent to provide a compound of formula (IIc)

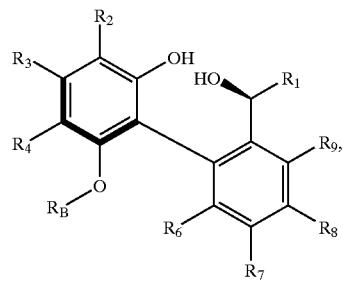
(IIc)

wherein $R_B$, $R_1$, $R_2$, $R_3$, $R_4$, $R_6$, $R_7$, $R_8$ and $R_9$ are as defined above; and
(d) treating the compound of formula (IIc) with an azo reagent and a phosphine reagent in a third solvent.

27. A process for the preparation of a compound having formula (I)

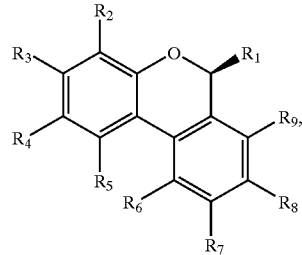
(I)

wherein
- $R_1$ is selected from the group consisting of alkenyl, alkyl, alkynyl and aryl;
- $R_2$, $R_3$ and $R_4$ are each independently selected from the group consisting of hydrogen, alkoxy, alkenyl, alkyl, alkynyl, aryl and halogen; or
- $R_2$ and $R_3$ or $R_3$ and $R_4$ together with the carbon atoms to which they are attached, together form a ring wherein the ring is selected from the group consisting of aryl, cycloalkyl and heterocycle;

$R_5$ is selected from the group consisting of hydrogen, alkenyl, alkenyloxy, alkoxy, alkoxycarbonyloxy, alkoxysulfonyloxy, alkyl, alkylcarbonyloxy, alkylsulfonyloxy, alkynyl, alkynyloxy, aryl, arylalkoxy, arylalkoxycarbonyloxy, aryloxy, arylsulfonyloxy, haloalkoxy, haloalkylcarbonyloxy, haloalkylsulfonyloxy, halogen, heterocycle and $(NR_CR_D)$carbonyloxy wherein $R_C$ and $R_D$ are each independently selected from the group consisting of hydrogen and alkyl; and $R_6$, $R_7$, $R_8$ and $R_9$ are each independently selected from the group consisting of hydrogen, alkoxy, alkenyl, alkyl, alkynyl, aryl and halogen; or $R_6$ and $R_7$ or $R_7$ and $R_8$ or $R_8$ and $R_9$ together with the carbon atoms to which they are attached, together form a ring wherein the ring is selected from the group consisting of aryl, cycloalkyl and heterocycle;

wherein said process comprises the steps of:

(a) treating a compound of formula (Ia) with at least two molar equivalents of a hydroxy deprotecting reagent in a first solvent to provide a compound of formula (Ia)

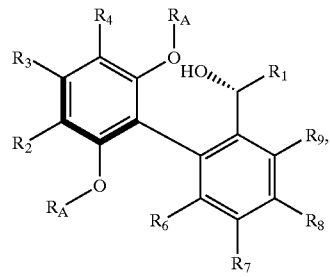

(Ia)

wherein $R_A$ is a hydroxy protecting group and $R_1$, $R_2$, $R_3$, $R_4$, $R_6$, $R_7$, $R_8$ and $R_9$ are as defined above, to provide a compound of formula (Ia) wherein $R_A$ is hydrogen;

(b) treating the product of step (a) with an azo reagent and a phosphine reagent in a second solvent to provide the compound of formula (I).

* * * * *